US010098367B2

(12) United States Patent
Jacobsen et al.

(10) Patent No.: US 10,098,367 B2
(45) Date of Patent: Oct. 16, 2018

(54) USE OF GLYCOSIDASE IN PREPARATION OF A MILK PRODUCT

(71) Applicant: Chr. Hansen A/S, Hoersholm (DK)

(72) Inventors: Jonas Jacobsen, Copenhagen (DK); Sandra Lykke Wind, Copenhagen NV (DK); Karsten Bruun Qvist, Frederiksberg C (DK)

(73) Assignee: Chr. Hansen A/S, Hoersholm (DK)

( * ) Notice: Subject to any disclaimer, the term of this patent is extended or adjusted under 35 U.S.C. 154(b) by 0 days.

(21) Appl. No.: 14/884,564

(22) Filed: Oct. 15, 2015

(65) Prior Publication Data

US 2016/0100599 A1 Apr. 14, 2016

Related U.S. Application Data

(63) Continuation of application No. 13/988,997, filed as application No. PCT/EP2011/070835 on Nov. 23, 2011, now Pat. No. 9,185,921.

(30) Foreign Application Priority Data

Nov. 23, 2010 (EP) ..................................... 10192207

(51) Int. Cl.
*A23C 9/12* (2006.01)
*A23C 9/123* (2006.01)
*A23C 9/127* (2006.01)
*A23C 11/10* (2006.01)
*A23C 19/032* (2006.01)

(52) U.S. Cl.
CPC ............ *A23C 9/1216* (2013.01); *A23C 9/123* (2013.01); *A23C 9/1275* (2013.01); *A23C 11/10* (2013.01); *A23C 11/103* (2013.01); *A23C 19/0328* (2013.01); *C12Y 302/01018* (2013.01); *C12Y 302/01022* (2013.01); *C12Y 302/01049* (2013.01); *C12Y 302/01096* (2013.01); *C12Y 305/01052* (2013.01)

(58) Field of Classification Search
CPC ...... A23C 9/1216; A23C 9/1275; A23C 9/123
USPC ......................................................... 426/42
See application file for complete search history.

(56) References Cited

U.S. PATENT DOCUMENTS

| 7,560,127 B2 | 7/2009 | Dambmann et al. |
| 2003/0113405 A1 | 6/2003 | Lynglev |
| 2004/0146603 A1 | 7/2004 | Dambmann et al. |
| 2005/0095316 A1 | 5/2005 | De Greeftrial et al. |
| 2005/0095317 A1 | 5/2005 | Queguiner et al. |
| 2007/0036883 A1 | 2/2007 | Schaffer et al. |
| 2013/0251848 A1 | 9/2013 | Jacobsen et al. |

FOREIGN PATENT DOCUMENTS

| EP | 1 489 135 A1 | 12/2004 |
| WO | WO-96/19582 A1 | 6/1996 |
| WO | WO-2007/095958 A1 | 8/2007 |
| WO | WO-2008/000895 A1 | 1/2008 |
| WO | WO-2008/037839 A1 | 4/2008 |
| WO | WO-2009/072904 A2 | 6/2009 |
| WO | WO-2012/069546 A1 | 5/2012 |

OTHER PUBLICATIONS

Cases, E. et al. 2003. J. Food. Sci. 68: 2406-2410.*
Thananunkul, D. et al. 1976. J. Food Sci. 41: 173-175.*
Farnwoth, E. R. et al. 2007. Int. J. Food Microbiol. 116: 174-181.*
Tamime, A. Y. et al. 1980. J. Food Protection. 43: 939-977.*
Ng. E.W. et al. 2011. Int. J. Food Microbiol. 145: 169-175.*
Bylund G., Dairy Processing Handbook, Tetra Pak Processing Systems AB, 1995. (Table of Contents).
Cases, E. et al., "Effect of k-Casein Deglycosylation on the Acid Coagulability of Milk", Journal of Food Science, vol. 68, Nr. 8, 2003.
Hassan, A.N. et al."Microstructure and Rheology of Yogurt Made with Cultures Differing Only in Their Ability to Produce Exopolysaccharides", J. Dairy Sci. 86: 1632-1638, Dec. 2002.
International Search Report in PCT/EP2011/070835 dated Apr. 18, 2012.
Kosikowski, F. et al. "Cheese and Fermented Milk Foods", 1982, Second Edition. (Table of Contents).
Minikiewicz, Piotr et al., "The Contribution of N-Acetylneuraminic Acid in the Stabilization of Micellar Casein", Pol. J Food Nutr. Sci., vol. 2/43, No. 3., Sep. 1993 pp. 39-48.
Notice of Allowance dated Jul. 22, 2015 issued in U.S. Appl. No. 13/988,997.
Office Action dated Feb. 27, 2015 issued in U.S. Appl. No. 13/988,997.
Office Action dated Aug. 26, 2014 issued in U.S. Appl. No. 13/988,997.
Scott, R., Cheesemaking Practice, Elsevier Applied Science Publishers, 2nd Edition, 1986. (Table of Contents).
Tamime and Deeth, "Yogurt: Technology and Biochemistry", Journal of Food Protection, vol. 23, No. 12, pp. 939-997, Dec. 1980.
Japanese Office Action dated Jun. 16, 2015 in application No. JP 2013-539300.
Agriculture & Livestock Industries Corporation, "An approach for coagulability of yogurt product," Aug. 2006, http://lin.alic.go.jp/alic/month/dome/2006/aug/chousa-1.htm.
Agriculture & Livestock Industries Corporation, "Livestock Information," Aug. 2006, http://lin.alic.go.jp/alic/month/dome/2006/aug/index2.htm.
Hugunin, U.S. Whey Ingredients in Yogurt and Yogurt Beverages, Applications Monograph Yogurt (U.S. Dairy Export Council, 2009), 12 pages.

* cited by examiner

*Primary Examiner* — Hamid R Badr
(74) *Attorney, Agent, or Firm* — Foley & Lardner LLP

(57) ABSTRACT

A method for making a milk product (e.g. a yogurt) comprising adding an effective amount of an N-linked glycosidase and/or an O-linked glycosidase to milk.

8 Claims, No Drawings

USE OF GLYCOSIDASE IN PREPARATION OF A MILK PRODUCT

CROSS REFERENCE TO RELATED APPLICATIONS

This application is a continuation of U.S. Ser. No. 13/988,997, filed May 22, 2013, which is the U.S. National Stage Entry of PCT/EP2011/070835, filed Nov. 23, 2011, which was published on May 31, 2012, as WO 2012/069546, which claims the benefit of EP Application No. 10192207.8, filed Nov. 23, 2010.

FIELD OF THE INVENTION

The present invention relates to a method for making a milk product (e.g. a yogurt) comprising adding an effective amount of an N-linked glycosidase and/or a O-linked glycosidase to milk.

BACKGROUND ART

Milk products such as e.g. fermented milk products (e.g. yogurt) are well known in the art.

As known in the art—properties such as viscosity and gel firmness are important properties for relevant milk products.

Generally speaking—if one can make more viscosity and/or gel firmness, using the same milk composition, one can make the same viscosity/gel firmness using less milk (or other) solids, thus saving on raw material (or obtaining a higher yield).

For low fat fermented milk products such as e.g. low fat yogurt it may be difficult to obtain an optimal preferred texture of the products—more precisely the problem may be to e.g. get a sufficient high texture viscosity in such low fat products.

Addition of protein, typically skim milk powder or whey based proteins, may be seen as a standard procedure to improve the texture in low fat yogurts. However, such a solution may be costly and does not fully comply with the concept of a low fat/low calories product since the added protein also contributes to the total energy content.

In relation to improvement of the texture—US2005/0095316A1 paragraph [0005] describes adding so-called texturing agents (thickeners, gelling agents) such as starch, pectin or gelatin. However, as known—to e.g. have extra pectin or gelatin in e.g. a yogurt product may not be preferred.

Within the last years so-called texturizing cultures, based on extracellular polysaccharides (EPS) production, have markedly improved the viscosity of such low fat milk products—for instance WO2007/095958A1 (Chr. Hansen A/S) describes that strains of *Streptococcus thermophilus* synthesize EPS that may give a desirable "ropy" or viscous texture to fermented milk products.

Accordingly, one may say that for e.g. low fat yogurt is the texture viscosity problem today as such pretty well solved by use of e.g. these EPC producing cultures.

However, as described in the article of A. N. Hassan et al (J. Dairy Sci: 86:1632-1638; 2003) the so-called gel firmness may decrease significantly when using such EPS producing cultures as compared to non EPS producing cultures.

Accordingly—one may say that the situation today is that for e.g. low fat yogurt products have the earlier viscosity problem essentially been solved by the use of the EPS producing cultures—however, the use of the EPS cultures may have "created" a new problem in relation to the decreased gel firmness.

In the article of A. N. Hassan et al is in the abstract referred to lower viscoelastic moduli—as known to the skilled person this viscoelastic moduli feature relates to gel firmness, in the sense that if the product has lower viscoelastic moduli it will have lower gel firmness.

In FIG. 1 of the article is shown that that shear stress of the EPS yogurts was much higher, which to a person skilled in the art directly translates to a higher viscosity.

As discussed above—for milk products in general such as e.g. fermented milk products (e.g. yogurt)—the so-called gel firmness is a very relevant property.

For instance, low gel firmness may give an undesirable mouth feel to the milk product.

Further, if e.g. a yogurt has a low gel firmness is will appear thin and flow too readily—e.g. on the spoon or e.g. in a bowl.

Further, if e.g. a yogurt has a low gel firmness it may be prone to syneresis (see below) due to whey separation.

As is well known in the art, milk clotting enzymes, such as the protease chymosin (alternatively named rennin) is used to make cheese, where chymosin causes coagulation and curd formation.

As is well known cheese making comprises three steps, or stages, that all come about as the result of addition of a milk clotting enzyme: 1) the formation of a clot (or soft gel), the solidification, or firming of this clot, and the eventual expulsion of whey, the latter process also called syneresis.

As evident—when making e.g. a yogurt one is generally not interested in getting this syneresis effect—i.e. the separation of the milk into solid curds and liquid whey.

Accordingly, use of a milk clotting enzyme like chymosin is generally not preferred when one wants to make e.g. a yogurt.

US2005/0095317A1 (Danone) describes the use of a protease with kappa-caseinolytic activity in the production fermented milk products such as yogurt.

The protease may e.g. be chymosin—see e.g. [0028] of the US patent application.

The proteases (e.g. chymosin) hydrolyse casein in the milk—accordingly one should prima facie have believed that the proteases (e.g. chymosin) could have given rise to a for yogurt production unwanted syneresis effect.

However, section [0008] explains that surprisingly and unexpectedly it was shown that use of proteases such as e.g. chymosin "improve the texture, and in particular to increase the viscosity of yogurts and fermented milks, without as a result inducing syneresis which would be unacceptable for such fermented dairy products".

US2005/0095316A1 (Danone) essentially relates to the same technical teaching as in US2005/0095317A1 (Danone) discussed above—however, in this US application the relevant proteases are defined as bacterial proteases (chymosin is from cows—i.e. it is not a bacterial protease).

U.S. Pat. No. 7,560,127B2 (DSM) describes use of special deglycosylation enzymes in cheese production. The deglycosylation enzymes are defined as enzymes that can deglycosylate the kappa casein (κ-casein) present in the milk. As discussed below—casein is a protein with so-called O-linked glycosylation. Accordingly, the deglycosylation enzymes mentioned in this US patent are enzymes that can deglycosylate O-linked glycosylated proteins such as kappa-casein (kappa-casein is a so-called O-linked glycoprotein).

The US patent reads on column 1, lines 51-58:

"It was surprisingly found that a deglycosylation of κ-casein will lead to clotting as it are the sugars associated with κ-casein that carry the negative charge which stabilize the casein micelles. Clotting of the milk in this way results in a process in which a larger part of the κ-casein is retained in the cheese and a higher yield can be obtained than using proteolytic activity of chymosin."

In short, one may say that this U.S. Pat. No. 7,560,127B2 patent essentially describes that one may get the, for cheese production, required clotting by using the mentioned O-linked related deglycosylation enzymes instead of chymosin. Since this U.S. Pat. No. 7,560,127B2 patent relates to production of cheese and in the claim 1 it is said that one may get the cheese without using a protease (such as chymosin) the skilled person will implicitly understand that the use of the O-linked related deglycosylation enzymes must lead to a substantial amount of syneresis.

It is here relevant to note that U.S. Pat. No. 7,560,127B2 relates to production of cheese, where a substantial amount of syneresis is required. Consequently, a skilled person would not expect it to apply to fermented milk product like yogurt, where syneresis is generally highly undesirable.

Further, U.S. Pat. No. 7,560,127B2 does not explicitly say anything about the herein relevant gel firmness property—i.e. one may say it only explicitly relates to the clotting/syneresis effect attributed to use of the described O-linked deglycosylation enzymes instead of chymosin.

The article of E. Cases et al (Journal of Food Science; Vol. 68, Nr. 8, 2003, Pages 2406-2410) describes deglycosylation of chemically acidified milk with an O-linked deglycosylation enzyme (neuraminidase; EC 3.2.1.18).

The milk is chemically acidified with the chemical GDL (see p. 2407, section "Acid milk coagulation")—accordingly, there is in the E. Cases et al article not described a "fermented milk" product inoculated with relevant microorganisms (e.g. a yogurt).

The article of E. Cases et al describes that the use of the O-linked deglycosylation enzyme neuraminidase (EC 3.2.1.18) gave higher final gel firmness to the enzymatically treated and chemically acidified milk.

It is here relevant to note that the article of E. Cases et al does not say anything of herein relevance with respect to the possible syneresis effect of using the O-linked deglycosylation enzyme neuraminidase (EC 3.2.1.18).

In the E. Cases et al article is not provided relevant evidence for the purity of the used neuraminidase (EC 3.2.1.18) O-linked deglycosylation enzyme preparation.

In view of this—it is submitted, that the enzyme preparation used may have comprised some relevant protease enzyme activity and that this protease enzyme activity could have been responsible for the described gel firmness effect—as discussed above, US2005/0095317A1 (Danone) describes that the use of a protease may improve the gel firmness.

The relevance of this suspicion is further underlined by that fact that *Clostridium perfringens*, the microorganism that the neuraminidase in the E. Cases et al. article was derived from (see Materials and Method section) is known to contain more than 140 proteolytic enzymes—see e.g. the authoritative Merops peptidase database (http://merops.sanger.ac.uk/cgi-bin/speccards?sp=sp000283; type=peptidase).

With no information on purity of the enzyme preparation provided, it thus seems very plausible that it was not purified to the exclusion of all relevant proteolytic enzymes that could in themselves have had the effect on gel firmness described in the E. Cases et al article.

As known in the art—the O-linked deglycosylation enzyme neuraminidase (EC 3.2.1.18) may also have some N-linked glycosidase activity. However, the E. Cases et al article discussed above only refers to the O-linked glycosidase activity of neuraminidase (EC 3.2.1.18) when herein relevant enzymatic activities of neuraminidase is discussed in he E. Cases et al article.

EP1489135A1 may be seen as relating to use of deglycosylated oleuropein (obtained from Olive leaf extracts) for increasing gel firmness of acidified whey milk and yogurt. Beta-glycosidase (beta-1,6-glucosidase) and lactase are in this document "simply" used to deglycosylate the oleuropein—i.e. the enzymes are here not the active component for increasing the gel firmness in the milk/yogurt. Oleuropein is not a protein/peptide with enzymatic activity. Beta-glycosidase is neither an N- nor O-linked glycosidase. The method of the present invention does preferably not comprise addition of an activated olive leaf extract (or other extracts) as disclosed in EP1489135A1 to an animal milk substrate.

SUMMARY OF THE INVENTION

The problem to be solved by the present invention may be seen in the provision of a new method to improve/increase the gel firmness of a relevant milk product—e.g. a fermented milk product like yogurt—in particular a low fat fermented milk product like a low fat yogurt. Further—the new method should preferably not negatively affect the viscosity of the product.

The solution is based on that the present inventors have identified that by use of a deglycosylation enzyme (i.e. a glycosidase) one can get a milk product (e.g. a yogurt) with significant increased/improved gel firmness. Further, the present inventors identified that use of herein relevant glycosidases may be done in a manner, wherein there is no significant syneresis effect—as discussed above, to have no significant syneresis effect is a big advantage e.g. in relation to making a fermented milk product such as an yogurt. In particular, in relation to use of O-linked glycosidase it was a surprise to the inventors that it could be used without a significant syneresis effect. The present inventors also identified that use of the deglycosylation enzyme does not negatively affect the viscosity of the product.

In working Example 4 herein is shown that use of the glycosidase PNGase-F gave a low fat yogurt with significant increased/improved gel firmness without any negative effect on the viscosity of the low fat yogurt.

As described in working Example 1 herein—the glycosidase enzyme preparations used in the working Examples herein were analyzed and found free of contaminants—i.e. they did not comprise contaminants such as protease enzyme activity.

It is here interesting to note that PNGase-F is a glycosidase that works on "N-linked glycans"—i.e. deglycosylate N-linked glycoproteins.

As discussed above—casein is a glycoprotein comprising O-linked glycans and PNGase-F can therefore as such not deglycosylate casein—accordingly, the reason for that PNGase-F gives the herein positive gel firmness result cannot as such be due to a mechanism relating to deglycosylation of casein as e.g. discussed in U.S. Pat. No. 7,560,127B2 (see above).

In summary and without being limited to theory—the fact that the present inventors demonstrated that a N-linked glycosidase like PNGase-F works in the present context (i.e.

gives improved gel firmness) illustrates that the basic mechanism behind getting the herein relevant improved gel firmness is completely different from the "deglycosylation of casein" based mechanism suggested in U.S. Pat. No. 7,560,127B2 with respect to use O-linked glycosidases as a substitute for chymosin in the preparation of cheese (see above).

Said in other words, one may say that the fact that a N-linked glycosidase like PNGase-F works in the present context (i.e. gives improved gel firmness) may be seen as highly surprising for a skilled person in view of the prior art such as e.g. U.S. Pat. No. 7,560,127B2.

Without being limited to theory—a possible explanation for that use of a glycosidase as such can give the herein relevant improved gel firmness is that the glycosidase removes glycans from relevant not casein whey proteins.

For instance, an N-linked glycosidase like PNGase-F may remove N-glycans from some of the whey glycoproteins such as α-lactalbumin which are known to be N-glycosylated. The whey proteins also to some extend engage in the protein-network, that gives rise to the property gel firmness.

Removal of hydrophilic glycans and charge changes imposed by the deamination reaction may favor the formation of a more rigid protein network and thereby one gets improved gel firmness.

Without being limited to theory—it is believed that some herein relevant whey glycoproteins also comprise O-linked glycans.

Accordingly, the present inventors tested if an O-linked glycosidase also could give the herein relevant improved gel firmness.

In working Example 5 herein is demonstrated that also use of an O-linked glycosidase like GalNAC can give the herein relevant improved gel firmness.

From a theoretically point of view—one would believe that a herein relevant advantage of using an N-linked glycosidase like PNGase-F would be a limited (or no) unwanted syneresis effect e.g. in relation to making a yogurt product.

One reason for this theoretically point of view is that a N-linked glycosidase like PNGase-F does not work on casein and as discussed in e.g. U.S. Pat. No. 7,560,127B2 one may get the, for cheese production, required clotting (syneresis) by using the mentioned O-linked related deglycosylation enzymes (to deglycosylate casein) instead of chymosin.

In working Example 4 herein was demonstrated that the N-linked glycosidase PNGase-F gave no herein unwanted syneresis effect in relation to making a yogurt.

The present inventors tested the herein unwanted syneresis effect in relation to e.g. making a yogurt for an O-linked glycosidase like GalNAC.

As shown in working Example 6 herein—one may say to the surprise of the present inventors—the there was no herein unwanted syneresis effect in relation to making a yogurt when the 0-linked glycosidase GalNAC was used for yogurt production.

In working Example 7 herein—is demonstrated that use of a glycosidase (here PNGase-F) gave the herein relevant improved gel firmness in both lactic acid bacteria (LAB) and chemical acidified milk.

Without being limited by theory, this suggests that the effect of the glycosidase on gel firmness is a physical effect (i.e. deglycosylation of whey proteins as discussed above)—rather than a biological effect (i.e. an effect, wherein the glycosidase essentially only affects something in relation to the functionality of the LAB as such).

In the working Examples discussed above were used already heat treated milk—i.e. the glycosidase enzyme was added to the milk after the relevant heat treatment.

Without being limited to theory—a glycosidase like e.g. PNGase-F should also work (i.e. give the herein relevant gel firmness improvement) when added to raw milk (i.e. not heat treated milk) followed by a herein relevant heat treatment.

Accordingly, an first aspect of the present invention relates to a method for making a milk product comprising the following step:

(i): adding a N-linked glycosidase and/or a O-linked glycosidase to a milk substrate; and (ii) optionally acidifying (e.g. fermenting) the milk substrate, and/or optionally performing adequate step(s) to get a milk product, wherein the adequate step(s) is/are performed under conditions, wherein the effective amount of the glycosidase gives—as a result of its presence—increased gel firmness to the dairy milk product.

The milk substrate may be selected for the group consisting of milk from animals (such as cows, sheep, ewes, goats, buffaloes or camels) and milk of plant origin (such as soy milk, oak milk, rice milk, almond milk).

An embodiment of the first aspect relates to a method for making a dairy animal milk product comprising following steps:

(i): adding an effective amount of a N-linked glycosidase and/or a O-linked glycosidase to an animal milk substrate; and (ii): performing adequate step(s) to get a dairy animal milk product, wherein the adequate step(s) is/are performed under conditions, wherein the effective amount of the glycosidase gives—as a result of its presence—increased gel firmness to the dairy milk product;

with the proviso that if the glycosidase is only an O-linked glycosidase (such as α-galactosidase, N-acetyl-galactosaminidase [GalNAC] and neuraminidase) capable of performing deglycosylation of κ-casein present in the milk then is the dairy animal milk product a fermented milk product inoculated with relevant microorganisms (a fermented milk product is not a cheese product with a significant elimination of milk serum).

The term "the effective amount of the glycosidase gives—as a result of its presence—increased gel firmness to the dairy milk product" of step (ii) of the first aspect may alternatively be termed "the effective amount of the glycosidase gives—as a result of its presence—improved gel firmness to the dairy milk product".

The term "performing adequate step(s) to get a milk product" of step (ii) shall be understood as relevant adequate step(s) to make a milk product of interest (e.g. a yogurt).

It is evident that the skilled person is perfectly aware of such adequate step(s)—that for instance in relation to making a yogurt comprises inoculation with suitable lactic acid bacteria (LAB) cultures.

It is routine work for the skilled person to measure gel firmness of a milk product of interest (e.g. a yogurt).

In working Example 2 herein is provided a suitable standard method for measurement of gel firmness of a milk product of interest—preferably the herein relevant gel firmness is measured according to the method of this Example 2.

The article of A. N. Hassan et al (3. Dairy Sci: 86:1632-1638; 2003) discussed above also describes a suitable standard method for measurement of gel firmness.

See e.g. the materials and method section of the article, where elastic modulus and viscoelastic modulus are determined—as can be seen in Example 2 herein, the parameters elastic modulus and viscoelastic modulus are used to determine gel firmness and from which one can optionally obtain the so-called complex modulus, as described in Example 2 herein.

Since it is easy for the skilled person to measure gel firmness of a milk product of interest—it is of course also easy for the skilled person to determine the requirement of step (ii) of the method of the first aspect relating to if:
"the effective amount of the glycosidase gives—as a result of its presence—improved gel firmness to the milk product".

In order to determine this requirement—the skilled person shall simply perform the "adequate step(s) to get a milk product" of step (ii) with and without presence of the effective amount of the glycosidase—and then determine the herein relevant gel firmness effect of the presence of the added amount of glycosidase.

If there is improved/increased gel firmness then there have been added an effective amount of the glycosidase to the milk substrate in accordance with step (i) of the first aspect and the adequate step(s) of step (ii) have also been performed under conditions, wherein the effective amount of the glycosidase gives—as a result of its presence—improved gel firmness to the dairy milk product.

As known to the skilled person—different methods to measure gel firmness may give different results in absolute values. However, in relation to measurement of improved gel firmness as discussed herein one is essentially measuring a relative improvement of the gel firmness—i.e. the improvement with and without presence of the effective amount of the glycosidase.

As understood by the skilled person—the method to measure gel firmness as e.g. described in working Example 2 herein and the article of A. N. Hassan et al will (within relatively minor measurement uncertainties) give the same relative results—i.e. independently of the specific measurement method used one will get the same result with respect to the relative improvement of the gel firmness.

The proviso of the method of the first aspect may be seen as a disclaimer in relation to above discussed U.S. Pat. No. 7,560,127B2 and above discussed article of E. Cases et al (Journal of Food Science; Vol. 68, Nr. 8, 2003, Pages 2406-2410).

As discussed above—there is in the E. Cases et al article not described a "fermented milk" product inoculated with relevant microorganisms (e.g. a yogurt).

As discussed above—U.S. Pat. No. 7,560,127B2 does not explicitly say anything about the herein relevant gel firmness property—i.e. one may say it only relates to the clotting/syneresis effect attributed to use of the described O-linked deglycosylation enzymes instead of chymosin.

However, one may say that by adding the in U.S. Pat. No. 7,560,127B2 described O-linked deglycosylation enzymes to a milk substrate during the process for making the cheese milk product—there could theoretically implicitly have been added an effective amount of glycosidase there maybe could have given a herein relevant improved gel firmness.

The proviso relates to the situation, wherein the glycosidase is only an O-linked glycosidase—U.S. Pat. No. 7,560, 127B2 does not describe anything of herein relevance in relation to use of N-linked glycosidase—accordingly, if the effective amount of a glycosidase (i.e. covering one or more glycosidase) added in step (i) of first aspect would be e.g. a mixture of a N-linked glycosidase and a O-linked glycosidase then it would not be a situation, wherein the glycosidase is only an 0-linked glycosidase.

In the present context—the skilled person can routinely identify if a milk product is a cheese product as described in U.S. Pat. No. 7,560,127B2 or another herein relevant milk product such as e.g. a fermented milk product like e.g. a yogurt.

Definitions

The term "glycan" refers to a polysaccharide or oligosaccharide. Glycans can be homo or heteropolymers of monosaccharide residues, and can be linear or branched. Glycan may also be used to refer to the carbohydrate portion of a glycoconjugate, such as a glycoprotein, glycolipid, or a proteoglycan.

The term "glycoproteins" are proteins that contain oligosaccharide chains (glycans) covalently attached to polypeptide side-chains. The carbohydrate is attached to the protein in a cotranslational or posttranslational modification.

The term "glycosidase" (also called glycoside hydrolase) refers to an enzyme that catalyzes the hydrolysis of the glycosidic linkage/bond—a glycosidic bond is a type of covalent bond that joins a carbohydrate (sugar) molecule to another group, which may or may not be another carbohydrate. A glycosidase that partially or completely deglycosylate N-linked glycans may herein be termed an N-linked glycosidase. Similarly, a glycosidase that partially or completely deglycosylate O-linked glycans may herein be termed an O-linked glycosidase.

The term N-linked glycosidase is a well defined term in the art and the skilled person knows if a specific glycosidase of interests is a N-linked glycosidase or not.

Similarly, the term O-linked glycosidase is a well defined term in the art and the skilled person knows if a specific glycosidase of interests is an O-linked glycosidase or not.

A glycosidase may herein also be termed a deglycosylation enzyme.

The term "glycosylation" is the enzymatic process that attaches glycans to proteins, lipids, or other organic molecules.

The term "N-linked glycans" refers to glycans attached to a nitrogen of normally asparagine or arginine side chains.

The term "O-linked glycans" refers to glycans attached to the hydroxy oxygen of normally serine, threonine, tyrosine, hydroxylysine, or hydroxyproline side chains, or to oxygens on lipids such as ceramide.

The term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria, The term "milk substrate" may be any raw and/or processed milk material that can be subjected to enzymatic treatment (and possibly fermentation) according to the method of the invention. Thus, useful milk substrates include, but are not limited to, solutions/suspensions of any milk or milk like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any animal (mammal) or non-animal source, e.g. being substantially pure milk, or reconstituted milk powder. Preferably, at least part of the protein in the milk substrate is proteins naturally occurring in milk, such as casein or whey protein. However, part of the protein may be proteins which are not naturally occurring in milk. Prior to fermentation, the milk substrate may be homogenized and pasteurized according to methods known in the art.

The term "milk" is to be understood as the lacteal secretion obtained by milking any mammal, such as cows, sheep, ewes, goats, buffaloes or camels. In a preferred embodiment, the milk is cow's milk. The term milk also comprises "milks" of non-animal or plant origin (eg from a vegetable or cereal source), such as soy milk, oak milk, rice milk, almond milk. Other sources are cotton, wheat, malt, corn, potato, bean, lupin, and sorghum. Optionally the milk is acidified, e.g. by addition of an acid (such as citric, acetic or lactic acid), or mixed, e.g. with water. The milk may be raw or processed, e.g. by filtering, sterilizing, pasteurizing, homogenizing etc, or it may be reconstituted dried milk. An important example of "bovine milk" according to the present invention is pasteurized cow's milk. It is understood that the milk may be acidified, treated with glycosidase, mixed or processed before, during and/or after the inoculation with bacteria.

In the present context, the term dairy product is a product made by treatment of a milk substrate with an N or O linked glucosidase, optionally the product is also fermented or acidified. The term includes fermented milk products (which can be drinkable, stirred or set) and cheeses.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Fermentation" in the methods of the present invention means the conversion of carbohydrates into alcohols or acids through the action of a microorganism. Preferably, fermentation in the methods of the invention comprises conversion of lactose to lactic acid.

Lactic acid bacteria, including bacteria of the species *Lactobacillus* sp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product. Such cultures are in general referred to as "starter cultures" or "starters".

Optionally, the fermented milk substrate may be subjected to heat treatment to inactivate the microorganism.

Fermentation processes to be used in production of fermented milk products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a fermented milk product.

In the present context, a yoghurt starter culture is preferably a bacterial culture which comprises at least one *Lactobacillus* strain, e.g. a *Lactobacillus bulgaricus* strain, and at least one *Streptococcus thermophilus* strain. In accordance herewith, a yogurt is a fermented milk product obtainable by inoculating and fermenting milk with a *Lactobacillus* strain and a *Streptococcus thermophilus* strain.

The term "spoonable" should be understood as to be consumed using a spoon. The term "spoonable milk product" includes stirred products. The term "stirred type product" specifically refers to a fermented milk product which sustains a mechanical treatment after fermentation, resulting in a destructuration and liquefaction of the coagulum formed under the fermentation stage. The mechanical treatment is typically but not exclusively obtained by stirring, pumping, filtrating or homogenizing the gel, or by mixing it with other ingredients.

The term "set-type product" includes a product based on milk which has been inoculated with a starter culture, e.g. a starter culture, and packaged next to the inoculating step and then fermented in the package.

The term "drinkable product" includes beverages such as "drinking yoghurt" and similar. The term "drinking yoghurt" typically covers a milk product produced by fermentation by the combination of *Lactobacillus* species and *Streptococcus thermophilus*. Drinking yoghurt typically has a milk solid non-fat content of 8% or more. Furthermore, the live culture count for drinking yoghurt drinks is typically at least 10E6 cell forming units (CFU) pr ml.

DETAILED DESCRIPTION OF THE INVENTION

Dairy Animal Milk Product

Generally speaking—the pH of a herein preferred milk product, including a dairy animal milk product (i.e. a product based on animal milk), is a pH from pH 3 to pH 6.5—more preferably from pH 3.5 to pH 5.75.

As know to the skilled person—one may get the relevant pH of a milk product by e.g. fermenting with a suitable lactic acid bacteria culture.

However, as known to the skilled person one may simply add a suitable acid (such as lactic acid) to get the required pH.

Alternative one may add a lactone (e.g. GDL lactone) to get the required pH or use other suitable known methods (e.g. enzymatic methods or pressureatiation with carbon dioxide) to get the required pH.

As discussed above—the use of a glycosidase to improve gel firmness as described herein may be particular useful in relation to so-called low fat milk products.

Accordingly, in a preferred embodiment the milk substrate used in step (i) of the method of the first aspect is a milk substrate with a low fat content—i.e. with a fat content of less than 3.5% fat, more preferably with a fat content of less than 1.5% and even more preferably with a fat content of less than 0.75%.

As discussed above—an advantage of the use of a glycosidase to improve gel firmness as described may be that one does not need to increase the protein content of e.g. a low fat milk product in order to get sufficient adequate gel firmness and thereby further minimizing the total calorific/energy content of the final low fat milk product (e.g. a low fat yogurt).

Accordingly, in a preferred embodiment the final milk product (e.g. yogurt) has a total calorific/energy content of less than 150 kilo calories per 100 g of milk product, more preferably the final milk product (e.g. yogurt) has a total calorific/energy content of less than 100 kilo calories per 100 g of the milk product.

As known—it is routine work for the skilled person to determine the calories content of a milk product of interest.

A suitable example of a milk product is a fermented milk product or a cheese.

In a preferred embodiment, the milk product is a fermented milk product.

In a preferred embodiment—the fermented milk product is at least one fermented milk product selected from the group consisting of: yogurt, alternate culture yogurt, butter milk, *acidophilus* milk, kefir, kumys and quark. Most preferably, fermented milk product is a yogurt.

In the present context—the terms "yogurt" and "fermented milk" have their usual meanings. In US2005/0095316A1 and US2005/0095317A1 (both Danone) are these terms defined in accordance with a relevant official decree/regulation in France—below is essentially referred to the same standard known definitions of these terms.

As known to the skilled person—to obtain a "yogurt or fermented milk" product it is in particular recalled that there must not be a significant elimination of milk serum and that there must be a heat treatment at least equivalent to pasteurization.

A suitable relevant heat treatment for making a fermented milk product such as e.g. a yogurt is, for example, a heat treatment of from 85 to 98° C. for 15 seconds to 30 minutes.

Because of the application of a heat treatment which is at least equivalent to standard pasteurization, milk serum proteins of the milk substrate are denaturated more or less (from 25 to 99% of them, approximately).

As evident to a skilled person—since there for a yogurt or fermented milk product "must not be a significant elimination of milk serum"—a yogurt or fermented milk product is not a cheese product as described in U.S. Pat. No. 7,560,127B2 (see above).

The term "fermented milk" relates to dairy product prepared with skimmed or unskimmed milks or skimmed or unskimmed, concentrated or powdered milks, enriched or not enriched with milk constituents, which has been subjected to heat treatment at least equivalent to pasteurization, inoculated with microorganisms belonging to the species that is or are characteristic of each product.

The amount of free lactic acid which they contain should preferably not be less than 0.6 gram per 100 grams at the time of sale to the consumer.

Fermented milks should preferably be kept, up to the time of sale to the consumer, at a temperature capable of preventing them spoiling.

The term "yogurt" denotes fermented milk obtained, according to fair and traditional practices, preferably by the development of specific thermophilic lactic acid bacteria only, such as e.g. *Lactobacillus delbrueckii* subsp. *bulgaricus* and *Streptococcus thermophilus*, which preferably should be inoculated simultaneously and preferably be live in the finished product, at a rate of preferably at least 10 million bacteria per gram expressed in relation to the milk-containing portion.

A fermented milk product is normally obtained by
(A): inoculating from $10^5$ to $10^{13}$ cfu/ml (preferably $10^6$ to $10^{11}$ cfu/ml) of lactic acid bacteria (LAB) culture to the animal milk substrate; and
(B): fermenting the milk substrate from 2 to 120 hours at a temperature from 10° C. to 55° C.

As known to the skilled person—suitable species of lactic acid bacteria include *Bifidobacterium*, *Lactobacillus* (such as *Lactobacillus delbrueckii* subsp. *bulgaricus*, *Lactobacillus acidophilus*, *Lactobacillus casei* or *Lactobacillus helveticus*), *Streptococcus* (such as *Streptococcus thermophilus*), *Lactococcus* (such as *Lactococcus lactis*), *Leuconostoc* (such as *Leuconostoc lactis*, *Leuconostoc mesenteroides*).

When the milk substrate is inoculated with a ferment made up of strains of *Lactobacillus delbrueckii* subsp. *bulgaricus* and of *Streptococcus thermophilus*, the product is generally understood to be a yogurt.

As known in the art—the term "alternate culture yogurt" refers to a fermented milk product made by using cultures of *Streptococcus thermophilus* and any *Lactobacillus* species.

As known in the art—the term "*acidophilus* milk" refers to a fermented milk product made by using culture of *Lactobacillus acidophilus*.

As known in the art—the term "Kefir" refers to a fermented milk product made by using starter culture prepared from kefir grains, *Lactobacillus kefiri*, species of the genera *Leuconostoc*, *Lactococcus* and *Acetobacter* growing in a strong specific relationship. Kefir grains constitute both lactose fermenting yeasts (*Kuyveromyces marxianus*) and non-lactose-fermenting yeasts (*Saccharomyces unisporus*, *Saccharomyces cerevisiae* and *Saccharomyces exiguus*).

As known in the art—the term "Kumys" refers to a fermented milk product made by using cultures of *Lactobacillus delbrueckii* subsp. *bulgaricus* and *Kluyveromyces marxianus*.

In a preferred embodiment—the milk product is a yogurt, wherein the yogurt is made by inoculation with a yogurt lactic acid bacteria culture that comprises *Lactobacillus delbrueckii* subsp. *bulgaricus* and *Streptococcus thermophilus* capable of synthesizing extracellular polysaccharides (EPS)—this preferred embodiment may be particular relevant if the yogurt is a low fat yogurt, i.e. wherein the milk substrate used in step (i) of the method of the first aspect is a milk substrate with a low fat content—i.e. with a fat content of less than 3.5% fat, more preferably with a fat content of less than 1.5% and even more preferably with a fat content of less than 0.75%.

As discussed above—the prior art describes a number of such strains of *Streptococcus thermophilus* that produce EPS—see e.g. WO2007/095958A1 (Chr. Hansen A/S).

Accordingly, the skilled person can routinely identify a number of such EPS producing strains and he can also routine identify if a specific strain of interest is capable of synthesizing EPS or not.

An example of a herein possible relevant theoretical business scenario could be that a company makes a milk concentrate/powder by use of a glycosidase as described herein and then sells this milk concentrate/powder to e.g. a yogurt producer that use this in their yogurt production to get a yogurt with improved/increased gel firmness—i.e. they may get the improved gel firmness without any extra addition as such of glycosidase during the yogurt production as such.

As understood by the skilled person—such a theoretical business scenario would be an example of a method within the scope of the method of the first aspect as discussed herein. The milk concentrate/powder may be seen as an example of a dairy animal milk product of the method of the first aspect. Further, as understood by the skilled person in the present context—the final yogurt will have the improved/increased gel firmness due to the previous addition of the glycosidase to the milk—i.e. the yogurt producer will also perform actions within the scope of the method of the first aspect as discussed herein.

Glycosidase

As discussed above—the term "glycosidase" (also called glycoside hydrolase) refers to an enzyme that catalyzes the hydrolysis of the glycosidic linkage/bond—a glycosidic bond is a type of covalent bond that joins a carbohydrate (sugar) molecule to another group, which may or may not be another carbohydrate.

As described above—a glycosidase may herein also be termed a deglycosylation enzyme.

The glycosidase may be a natural glycosidase or it may be a variant/mutated of a natural glycosidase—as known to the skilled person, one may make mutated variants of a enzyme of interest (here a glycosidase) to e.g. improve the stability of the enzyme while maintaining the key enzymatic activity (here glycosidase activity) of the enzyme.

In order to e.g. get a minimum of unwanted syneresis (in particular if the milk product is a fermented milk product such as a yogurt)—it may be preferred that the glycosidase is an N-linked glycosidase.

As discussed above, the term N-linked glycosidase is a well defined term in the art and the skilled person knows if a specific glycosidase of interests is a N-linked glycosidase or not. Further the prior art describes a number of different herein suitable N-linked glycosidases.

Examples of a herein suitable N-linked glycosidase may be at least one glycosidase selected from the group consisting of: Peptide-N(4)-(N-acetyl-beta-glucosaminyl)asparagine amidase (EC number: 3.5.1.52; alternative names: N-Glycosidase-F or PNGase-F) and Endo-β-N-acetylglucosaminidase H (EC number: 3.2.1.96; alternative name ENDO-H).

The immediately above described N-linked glycosidases may in the present context be described as glycosidases that have N-linked glycosidase activity and no herein significant O-linked glycosidase activity.

Accordingly, it may herein be preferred that the N-linked glycosidase is an N-linked glycosidase that have no herein relevant O-linked glycosidase activity (such as no O-linked glycosidase activity).

The N-Glycosidase-F, also known as PNGase-F, used in the process, is an asparagine amidase (EC 3.5.1.52) that may be derived from *Flavobacterium mesingosepticum*. It catalyses the complete and intact cleavage of N-linked oligosaccaharides from glycoproteins. It may be derived as a commercial product from New England Biolabs Inc. under the name PNGase-F or produced recombinantly in a strain like *Escherichia coli* as we have done using the plasmid and method described in working Example 1 herein.

Endo-β-N-acetylglucosaminidase H (EC 3.2.1.96), also known as ENDO-H, may be derived from *Streptomyces plicatus*. ENDO-H catalyses the hydrolysis of the glycosidic bond between the two N-acetylglycosamines of N-linked glycosylations. It may be derived as a commercial product from New England Biolabs Inc. under the name ENDO-H.

Examples of a herein suitable O-linked glycosidase may be at least one glycosidase selected from the group consisting of: α-N-acetyl-galactosaminidase (EC number: 3.2.1.49; alternative name: GalNAC); α-galactosidase (EC number: 3.2.1.22); and neuraminidase (EC number: 3.2.1.18).

GalNAC is a highly specific exoglycosidase that catalyzes the hydrolysis of α-linked D-N-acetyl-galactosamine residues from. It may be derived as a commercial product from New England Biolabs Inc.

As discussed above, the term O-linked glycosidase is a well defined term in the art and the skilled person knows if a specific glycosidase of interests is a O-linked glycosidase or not. Further the prior art describes a number of different herein suitable O-linked glycosidases.

The effective amount/activity of a glycosidase is herein determined according to the art.

According to the art—for a N-linked glycosidase (such as e.g. PNGase-F and Endo-H) one activity unit is defined as the amount of enzyme required to remove >95% of the carbohydrate from 10 μg of denatured RNase-B in 1 hour at 37° C. in a total reaction volume of 10 μl.

For GalNAC (an O-linked glycosidase) one activity unit is defined as the amount of enzyme required to cleave >95% of the terminal α-D-N-acetyl-galactosamine from 1 nmol (GalNAcα1-3)(Fucα1-2)Galα1-4Glc-7-amino-4-methyl-coumarin (AMC), in 1 hour at 37° C. in a total reaction volume of 10 μl.

A number of herein relevant glycosidase enzymes are commercially available from the company New England Biolabs—reference is also made to the product catalogue New England Biolabs (as e.g. available on-line on their web-page) for further details in relation to specific standard definitions of herein relevant glycosidase activity units.

Step (i) of the Method of First Aspect

Step (i) of the herein described method of the first aspect reads: "(i): adding an effective amount of an N-linked glycosidase and/or an O-linked glycosidase to an animal milk substrate".

As understood by the skilled person in the present context—the N-linked glycosidase and/or an O-linked glycosidase is normally added to the animal milk substrate as a substantial pure glycosidase composition—e.g. a glycosidase composition, wherein the glycosidase activity represents at least 5% of the total enzymatic activity of the glycosidase composition as such.

It may be a glycosidase composition, wherein the glycosidase activity represents at least 25% of the total enzymatic activity of the glycosidase composition or a glycosidase composition, wherein the glycosidase activity represent at least 50% of the total enzymatic activity of the glycosidase composition.

Many times if would be preferred that such a substantial pure glycosidase composition is a glycosidase composition, wherein the glycosidase activity represent at least 90% of the total enzymatic activity of the glycosidase composition.

An effective amount of a glycosidase may be one specific type of a glycosidase (e.g. PNGase-F) or be a mixture of herein relevant glycosidase enzymes (e.g. two different N-linked glycosidases or one N-linked and one O-linked glycosidase).

When there herein is said that it may be preferred that the glycosidase added in step (i) of the method of the first aspect is a N-linked glycosidase it of course means that there must be added an effective amount of a N-linked glycosidase in step (i) and this N-linked glycosidase gives—as a result of its presence—improved gel firmness to the dairy milk product.

However, when said that N-linked glycosidase is preferred it does of course not mean that there must not be added any O-linked glycosidase in step (i).

The same applies when herein is said that O-linked glycosidase is preferred—i.e. here there must be added O-linked glycosidase in step (i)—but there may also be added N-linked glycosidase.

To the contrary and as evident to the skilled person—when there herein is said that the glycosidase is only an O-linked glycosidase then there must not be added N-linked glycosidase in step (i) of the first aspect. The same applies when herein is said the glycosidase is only an N-linked glycosidase then there must not be added O-linked glycosidase in step (i) of the first aspect.

As known in the art—a dairy milk product is generally given a heat treatment. As known in the art—heat treatment typically uses temperatures below boiling since at very high temperatures, casein micelles will irreversibly aggregate (or "curdle").

In the present context—the term "pasteurized" in relation to a pasteurized dairy animal milk product refers to a standard pasteurization step (i.e. involving a suitable heat treatment of the milk). In the present context—it is evident that the skilled person knows if a specific milk product of interest is a pasteurized dairy animal milk product or not.

As understood by the skilled person—a standard pasteurization step may be heat treatment of around 71-72° C. for around 15-20 seconds As discussed above—to obtain a "yogurt or fermented milk" product it is in particular recalled that there must not be a significant elimination of milk serum and that there must be a heat treatment at least equivalent to pasteurization.

A suitable relevant heat treatment for making a fermented milk product such as e.g. a yogurt is, for example, a heat treatment of from 85 to 98° C. for 15 seconds to 30 minutes.

Depending on the type of heat treatment used—the heat treatment may e.g. be a heat treatment of the milk by using a temperature from 65 to 150° C. for a fraction of a second to 30 minutes.

As discussed above—when the milk product is a fermented milk product such as e.g. a yogurt there must be a heat treatment at least equivalent to pasteurization.

The glycosidase may in step (i) be added before or after the heat treatment step—i.e. the heat treatment of the milk by using a temperature from 65 to 150° C. for a fraction of a second to 30 minutes.

In some cases it may be preferred that that glycosidase is added to already heat treated milk. As discussed above—when the milk product is a fermented milk product the milk substrate is inoculated and fermented with a relevant lactic acid bacteria (LAB) culture.

When the milk product is a fermented milk product—the glycosidase may be added before, together or after the inoculation of the milk substrate with the lactic acid bacteria (LAB) culture.

In relation to milk product in general—it may preferred that the glycosidase is added before the pH of the milk substrate gets below pH 6.

In relation to a fermented milk product—it is preferred that the glycosidase is added before the relevant lactic acid bacteria fermentation process has ended—i.e. preferably before the pH of the milk substrate gets below pH 6.

It is herein believed that addition of from 10 activity units per ml milk to 1000 activity units per ml milk of glycosidase is enough to get a herein relevant effective amount of a glycosidase—i.e. enough to get a herein relevant improved gel firmness.

If relevant for a specific purpose—one may add more glycosidase e.g. up to 20000 activity units per ml milk of glycosidase.

As discussed above—the effective amount/activity of a glycosidase is herein determined according to the art.

Step (ii) of the Method of First Aspect

Step (ii) of the herein described method of the first aspect reads: "(ii): performing adequate step(s) to get a dairy animal milk product, wherein the adequate step(s) is/are performed under conditions, wherein the effective amount of the glycosidase gives—as a result of its presence—improved gel firmness to the dairy milk product"

As discussed above—performing adequate step(s) to get a dairy animal milk product of interest is routine work for the skilled person—e.g. if the milk product is e.g. a yogurt, the skilled person of course knows the adequate step(s) to get yogurt of interest.

In relation to the conditions, wherein the effective amount of the glycosidase gives improved gel firmness to the dairy milk product—it is evident that these conditions shall be conditions, wherein the glycosidase enzyme as such is active during a sufficient time period.

As shown in the working Examples herein—the present inventors have identified that a number of different glycosidase enzymes have a suitable activity during normal suitable conditions (e.g. temperature, pH etc) for making a herein relevant milk product such as a yogurt.

In short and as understood by the skilled person—the preferred conditions to get preferred herein relevant glycosidase activity will depend on the specific glycosidase enzyme(s) used (e.g. PNGase-F) and the specific milk product to be made (e.g. a yogurt).

In the present context—examples of suitable reaction conditions for the glycosidase to give the herein relevant improved gel firmness could be:

Temperature from 10 to 50° C. (such as from 20 to 40° C.);

pH from pH 3 to pH 9 (such as from pH 4 to pH 7.5, from 3 to 7 or from 3 to 6.5);

a time period from 10 minutes to 120 hours (such as from 1 hour to 120 hours, or from 0.5 to 5 hours)

In a preferred embodiment, the presence of the glycosidase in step (ii) gives a 1.25 times improved gel firmness to the dairy milk product; more preferably a 1.50 times improved gel firmness to the dairy milk product and even more preferably the presence of the glycosidase in step (ii) gives a 1.7 times improved gel firmness to the dairy milk product.

As discussed above—the present inventors identified that use of the glycosidase does not negatively affect the viscosity of the final milk product.

Accordingly, in a preferred embodiment—step (ii) is performed under conditions, wherein the effective amount of the glycosidase gives—as a result of its presence—no negative effect on the viscosity to the dairy milk product.

It is routine work for the skilled person to measure viscosity of a milk product of interest (e.g. a yogurt).

In working Example 2 herein is provided a suitable standard method for measurement of viscosity of a milk product of interest—preferably the herein relevant viscosity is measured according to the method of this Example 2.

The article of A. N. Hassan et al (J. Dairy Sci: 86:1632-1638; 2003) discussed above also describes a suitable standard method for measurement of viscosity.

See e.g. the materials and method section and FIG. 1 of the article, where shear stress is determined—as can be seen in Example 2 herein, the parameter shear stress is used as a measure of viscosity.

Since it is easy for the skilled person to measure viscosity of a milk product of interest—it is of course also easy for the skilled person to determine the preferred embodiment of step (ii) of the method of the first aspect relating to if:

"step (ii) is performed under conditions, wherein the effective amount of the glycosidase gives—as a result of its presence—no negative effect on the viscosity to the dairy milk product".

In order to determine this requirement—the skilled person shall simply perform the "adequate step(s) to get a milk product" of step (ii) with and without presence of the effective amount of the glycosidase—and then determine the herein relevant viscosity effect of the presence of the added amount of glycosidase.

As can be seen in the working Examples herein—one may actually get an improved viscosity by using a glycosidase as described herein.

Accordingly, in a preferred embodiment, the presence of the glycosidase in step (ii) gives a 1.10 times increased viscosity to the dairy milk product; more preferably a 1.20 times increased viscosity to the dairy milk product.

As understood by the skilled person—the method to measure viscosity as e.g. described in working Example 2 herein and the article of A. N. Hassan et al will (within relatively minor measurement uncertainties) give the same relative results—i.e. independently of the method used one will get the same result with respect to the relative improvement of the viscosity.

As discussed above—in working Examples herein was demonstrated that both N-linked and O-linked glycosidase gave no herein unwanted syneresis effect in relation to making a yogurt.

Accordingly, in a preferred embodiment step (ii) is performed under conditions, wherein the effective amount of the glycosidase gives—as a result of its presence—no increase in the syneresis effect to the dairy milk product.

This—no increase in the syneresis effect—is particular relevant when the dairy milk product is a fermented milk product such as e.g. a yogurt.

It is routine work for the skilled person to measure syneresis effect of a milk product of interest (e.g. a yogurt).

In working Example 3 herein is provided a suitable standard method for measurement of syneresis of a milk product of interest—preferably the herein relevant syneresis is measured in accordance with the method of this Example 3.

Essentially, the standard method to measure syneresis effect of Example 3 is based on a proper relevant storage of a milk product of interest and measurement of the amount of whey on top of the milk product of interest.

Since it is easy for the skilled person to measure syneresis of a milk product of interest—it is of course also easy for the skilled person to determine the preferred embodiment of step (ii) of the method of the first aspect relating to if: "step (ii) is performed under conditions, wherein the effective amount of the glycosidase gives—as a result of its presence—no increase in the syneresis effect to the dairy milk product".

In order to determine this requirement—the skilled person shall simply perform the "adequate step(s) to get a milk product" of step (ii) with and without presence of the effective amount of the glycosidase—and then determine the herein relevant syneresis effect of the presence of the added amount of glycosidase.

Also, the present invention relates to a method for producing a milk product, said method comprising:
a) providing a milk substrate;
b) treating the milk substrate with an enzyme having N-linked glycosidase activity; and
c) optionally fermenting the milk substrate with a microorganism, such as a lactic bacterium.

In an interesting embodiment, step b) is performed before or during step c).

As discussed above, the milk substrate may origin from any animal or non-animal source.

The milk product is preferably produced substantially without, or completely without any addition of a thickener and/or stabilizer, such as pectin, gelatin, starch, modified starch, carrageenan, alginate, and guar gum.

In an interesting embodiment, the microorganism is a lactic acid bacterium and/or a microorganism which produces a polysaccharide, such as an exopolysaccharide (EPS).

The microorganism may be a lactic acid bacterium, and preferably belong to a species selected from the group consisting of: *Streptococcus thermophilus, Lactobacillus delbrueckii* subsp. *Bulgaricus, Lactococcus lactis, Lactococcus lactis* subsp. *cremoris, Leuconostoc mesenteroides* subsp. *cremoris, Pseudoleuconostoc mesenteroides* subsp. *cremoris, Pediococcus pentosaceus, Lactococcus lactis* subsp. *lactis* biovar. *diacetylactis, Lactobacillus casei* subsp. *Casei, Lactobacillus paracasei* subsp. *Paracasei, Bifidobacterium bifidum*, and *Bifidobacterium longum*.

Interesting embodiments of any method of the present invention are:
A method wherein the milk substrate is subjected to pasteurization before acidification and the enzyme treatment is performed before pasteurization;
A method wherein the milk substrate is subjected to heat treatment prior to treatment with the enzyme having N-linked glycosidase activity;
A method wherein the milk product is selected from the group consisting of: a set-type fermented milk product, a drinkable fermented milk product, and a spoonable fermented milk product;
A method wherein the milk product has a milk solid non-fat content of less than 8%;
A method wherein the milk product has a fat content of less than 2%;
A method wherein the milk product has a fat content of less than 0.5%;
A method wherein the milk product is packaged (ie the method comprises packaging); and/or
A method wherein the glycosidase is selected from the group consisting of: α-N-acetyl-galactosaminidase; GalNAC); α-galactosidase; neuraminidase; Peptide-N (4)-(N-acetyl-beta-glucosaminyl)asparagine amidase; N-Glycosidase-F; PNGase-F; Endo-β-N-acetylglucosaminidase H; ENDO-H and any enzyme classified in EC 3.2.1.49, EC 3.2.1.18, EC 3.2.1.22, EC 3.5.1.52, or EC 3.2.1.96.

In the present context, the term "packaging" (a suitable amount of) the product in a suitable package relates to the final packaging of the product to obtain a product in distributable form so that the product can be ingested by e.g. a person or a group of persons. A suitable package may thus be a bottle, container, package or similar, and a suitable amount may be e.g. 10 ml to 5000 ml, but it is presently preferred that the amount in a package is from 50 ml to 1000 ml. Such a packaged product is a part of the present invention.

In a further aspect, the present invention also relates to a milk product obtainable by a method of the present invention.

In yet a further aspect, the present invention relates to a milk product which is obtainable by a method comprising adding an N-linked glycosidase and/or a O-linked glycosidase to a milk substrate. The glycosidase should be added in "an effective amount" to give the desired gel stiffness.

The milk products of the invention may have been fermented by inoculation with a lactic acid bacteria culture, prior to and/or during and/or after the treatment with the glycosidase.

The milk product may be packaged, e.g. in a sealed container having a volume in the range of 10 ml to 5000 ml, such as in a container having a volume of 25 ml to 1500 ml or a volume of 50 ml to 1000 ml.

In a further aspect, the present invention relates to the use of an N-linked glucosidase in a method for preparation of a milk product, such as a fermented milk product (such as yoghurt) or cheese (such as fresh cheese, fromage frais, quark, etc).

Also, the present invention relates to the use of an N-linked glucosidase in a method for improving the texture (such as gel firmness or stiffness) of a milk product, such as a fermented milk product (such as yoghurt) or cheese (such as fresh cheese, fromage frais, quark, etc).

In a presently preferred embodiment, the invention relates to the use of an enzyme having N-linked and/or O-linked glycosidase activity for improving the mouth feel of a milk product, such as yoghurt.

The use may comprise that the milk product has been produced using a lactic acid bacterium which produces a polysaccharide, such as an exopolysaccharide (EPS).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXAMPLES

Example 1: Glycosidases

The examples of glycosidases used in the method of as described herein is an asparagine amidase, an acetylglucosaminidase or a galactosaminidase.

The N-Glycosidase-F, also known as PNGase-F, used in the process, is an asparagine amidase (EC 3.5.1.52) which may be derived from *Flavobacterium mesingosepticum*. It catalyses the complete and intact cleavage of N-linked oligosaccharides from glycoproteins. It may be obtained as a commercial product from New England Biolabs Inc. under the name PNGase-F or produced recombinantly in a strain like *Escherichia coli* as we have done using the plasmid and method described in Loo et at (Protein Expression and Purification 24, 90-98, 2002).

Endo-β-N-acetylglucosaminidase H (EC 3.2.1.96), also known as ENDO-H, may be derived from e.g. *Streptomyces plicatus*. ENDO-H catalyses the hydrolysis of the glycosidic bond between the two N-acetylglycosamines of N-linked glycosylations. It may be obtained as a commercial product from New England Biolabs Inc. under the name ENDO-H.

α-N-acetyl-galactosaminidase (EC 3.2.1.49) is a highly specific exoglycosidase that catalyzes the hydrolysis of α-linked D-N-acetyl-galactosamine residues from threonines or serines. It may be obtained as a commercial product from New England Biolabs Inc. under the name the name α-N-acetyl-galactosaminidase.

For the in-house produced PNGase-F we have confirmed a high grade (>95%) of purity using Sodium dodecyl sulfate-polyacrylamide gel electrophoresis (SDS-PAGE) followed by coomassie brilliant blue (CBB) staining. To further confirm the purity the pooled enzyme was separated by SDS-PAGE and stained using silver. Appearing bands were next analyzed by mass-spec analysis which confirmed the presence of PNGase-F and only PNGase-F.

Potential a-specific proteolytic activity of the in-house purified PNGase-F was evaluated in a proteolytic assay using bovine-kappa-casein (Sigma-Aldrich) as a substrate. In this assay we tested the proteolytic activity at various pH values resembling the natural pH drop occurring in yogurt fermentation. To challenge the system we utilized a 20 fold higher enzyme concentration than in the process of the invention and incubated four hours at each pH-value. Under these conditions we did not find any evidence of a-specific proteolytic activity.

Conclusions:

Based on the results discussed above—it was clear that the so-called in-house produced PNGase-F was free of contaminants.

The other commercially available glycosidases discussed above were also free of contaminants as described by the supplier.

Example 2: Method for Measuring Gel Firmness and Viscosity

Gel firmness was measured by the use of an Anton Paar rheometer with an automatic sample changer (Physica DSR Rheometer+ASC). The measuring bob was placed in the measuring cup containing 20 ml sample, which had been stirred by the hand and heated to 13° C. After the bob had been placed in the sample a wait time was applied. Next, gel firmness was measured by oscillation. Here the strain was kept constant at 0.3% and the frequency was increased from 0.5 Hz to 30 Hz. From the measurement the elastic modulus (G') and the viscous modulus (G") could be calculated, and from these the complex modulus (G*) was obtained:

$$G^* = \sqrt{G'^2 + G''^2}$$

G* at 1 Hz was then used as a measure of the gel firmness and used for comparison of the different samples.

Using the same equipment (Anton Paar rheometer) the viscosity was measured by increasing the shear rate from 0.2707 1/s to 300 1/s with measuring points (shear stress) every 10 s. The shear rate was then decreased from 275 1/s to 0.2707 1/s with measuring points every 10 s. Shear stress at 300 1/s was then used as a measure of the viscosity of the product.

Conclusions:

Based on above standard methods for measuring gel firmness and viscosity—it is routine work for the skilled person to determine if there has been an improvement of the gel firmness and/or viscosity to a dairy milk product of interests by addition of a glycosidase according the method for making a dairy animal milk product as described herein.

Example 3: Methods for Measuring Syneresis

Two different methods for measuring the amount of syneresis have been used in the invention:

Method 1:

50 ml yogurt (produced like in example 4) is put into an Eppendorf tube and placed in cold storage (5° C.) for 14 days, after which the amount of whey on top of the yogurt is measured with a ruler (in mm).

As evident to the skilled person—one may also measure the syneresis effect of another milk product than yogurt by storage of a milk product of interest and measure the amount of whey on top of the milk product of interest.

Method 2:

Skim milk was fortified with 2% skim milk powder (SMP, producer?) and placed in the refrigerator overnight. The batch was heat treated for 20 minutes at 90° C. 75 ml milk solution was put into a 100 ml volumetric flask together with 0.02% YoFlex® Advance 2.0 yogurt culture (may be obtained from Chr. Hansen A/S, Denmark) and enzyme (either PNGase or GalNAC). The total weight of the milk, culture and enzyme was noted. The solution was heated to 43° C. and fermented to pH 4.55 after which the flasks were put in cold storage for 7 days. After 7 days the whey on top of the yogurt was poured of and weighed. The amount of syneresis can hereafter be calculated as a percentage.

As evident to the skilled person—one may also measure the syneresis effect of another milk product than yogurt by e.g. fermenting with another not yogurt culture of interest, storage and measure the amount of whey on top of the milk product of interest.

Conclusions:

Based on above standard methods for measuring syneresis effect—it is routine work for the skilled person to determine if there has been a significant syneresis effect to a dairy milk product of interests by addition of a glycosidase according the method for making a dairy animal milk product as described herein.

Example 4: Effect of PNGaseF on Gel Firmness (2 l Scale)

2 liters of skim milk (0.1% fat, Arla Express, Slagelse) was fortified with 1.6% skim milk powder (SMP, producer?) and placed in the refrigerator overnight. The solution was heat treated for 20 minutes at 90° C., cooled down to 43° C., inoculated with 0.02% YoFlex® Advance 2.0 (obtained from Chr. Hansen A/S, Denmark) and either 10 ml PNGase-F or in the reference sample 10 ml 20 mM Na-phosphate buffer pH 7.5 containing 50 mM NaCl and fermented to pH 4.55. When pH 4.55 was reached, the yogurt was stirred and passed through a post treatment unit (PTU), which subjects the yogurt to a back pressure of 2 bars at 25° C. The final product was subjected to rheometer analysis on day 5.

TABLE 1

Experimental results of a 2 l scale experiment of the preparation of a low fat yogurt in the absence and presence of in-house PNGase-F

| | Complex Modulus (Pa) | Shear stress at (300 1/s) | Syneresis (mm) |
|---|---|---|---|
| Advance 2.0 | 29.2 ± 0.86 | 63.7 ± 0.61 | 8 |
| Advance 2.0 + PNGase-F (250 U/ml milk) | 51.0 ± 0.57 | 70.7 ± 0.2 | 4 |

For the N-glycosidases one activity unit is defined as the amount of enzyme required to remove >95% of the carbohydrate from 10 µg of denatured RNase-B in 1 hour at 37° C. in a total reaction volume of 10 µl The numbers in table 1 show that PNGase-F increases the gel firmness of a low fat yogurt. Under these conditions with 75% compared to the reference. The viscosity obtained in the presence of PNGase-F is comparable or slightly better than the reference sample. In data not shown here we found that the increase in gel firmness in response to PNGase-F treatment was dose dependent. We also evaluated syneresis using method 1 from Example 3 and found that the syneresis was reduced in response to PNGase-F treatment.

Conclusions:

The results above demonstrated that PNGase-F increases the gel firmness of a low fat yogurt. Under the conditions of this experiment with 75% (i.e. 1.75 times) compared to the reference. Further was found that the syneresis was reduced in response to PNGase-F treatment.

The viscosity obtained in the presence of PNGase-F is comparable or slightly better than the reference sample.

Example 5: Testing of Different Glycosidases in Low Fat Yogurt

Yogurts were made directly in 20 ml rheometer cups. Hereby a set-yogurt was obtained. Skim milk (0.1% fat, Arla Express, Slagelse) was fortified with 2% skim milk powder (SMP) and placed in the refrigerator overnight. The solution was heat treated for 20 minutes at 90° C., cooled down to 43° C., inoculated with 0.02% YoFlex® Advance 2.0 and different deglycosidases and fermented (Table 1)

The samples were then placed in the refrigerator and the rheology was measured at day 3 according to example 2.

TABLE 2

Experimental result of a 20 ml cup lab scale experiment of the preparation of a low fat yogurt in the presence and absence of commercially obtained deglycosidases. All tested enzymes in this table were obtained from New England Biolabs Inc.

| | Concentration (U/ml milk) | Gel firmness (Pa) |
|---|---|---|
| Advance 2.0 + PNGase-F | 250 | 608 ± 32.5 |
| Advance 2.0 + Endo-H | 250 | 564 ± — |
| Advance 2.0 + α-N-Acetyl galactosaminidase | 50 | 482 ± 19.8 |
| Advance 2.0 | 0 | 391 ± 7.5 |

For N-glycosidases PNGase-F and Endo-H one unit is defined as in Table 1. For α-N-Acetyl-galactosaminidase, an O-glucosidase, one unit is defined as the amount of enzyme required to cleave >95% of the terminal α-D-N-acetyl-galactosamine from 1 nmol (GalNAcα1-3)(Fucα1-2)Galα1-4Glc-7-amino-4-methyl-coumarin (AMC), in 1 hour at 37° C. in a total reaction volume of 10 µl.

For all tested glycosidases, N-glucosidases as well as the O-glucosidase GalNAC, the gel firmness was found to be improved markedly. At the tested concentrations PNGase-F obtained commercially was found to have the most potent effect on the gel firmness of the low fat yogurt.

Conclusions:

The results above demonstrated that for all tested glycosidases, N-glucosidases as well as the O-glucosidase GalNAC, the gel firmness was found to be improved markedly.

Example 6: Syneresis Experiment Using a Glycosidase Working on O-Linked Glycosylations In U.S. Pat. No. 7,560,127 it was shown that the α-glucosidase GalNAC could lead to cheese curd/clotting formation. We here analyzed what effect GalNAC had on syneresis formation in low fat yogurt. The experiment was conducted as described in Example 3 Method 2. Yogurts were made directly in 100 ml rheometer cups. Hereby a set-yogurt was obtained. Skim milk (0.1% fat, Arla Express, Slagelse) was fortified with 2% skim milk powder (SMP, Aria Express, Slagelse) and placed in the refrigerator overnight. The solution was heat treated for 20 minutes at 90° C., cooled down to 43° C., inoculated with 0.02% YoFlex® Advance 2.0 and GalNAC at a concentration of 100 U/ml of milk. For the reference sample without enzyme the percentage of whey after 21 days was 0.3±0.04% whereas the whey fraction for the enzyme treated sample was 0.2±0.08%. Surprisingly, it was therefore found that treatment with GalNAC did not increase the syneresis when compared to a reference sample fermented with the same culture. This result was unexpected since U.S. Pat. No. 7,560,127 would indicate that removal of O-linked glycans leads to curd formation and thus separation of the whey.

Conclusions:

The results above demonstrated that the tested O-linked glycosidase did not increase the syneresis during the production of the yogurt.

Example 7: LAB and Chemically Acidified Milk

In the current example we wanted to assess whether or not the effect of PNGase-F was dependent on the mechanism of acidification. Experimentally this was addressed by comparing the effect of PNGase-F on a fermented yogurt and a yogurt acidified chemically with Glucono-δ-lactone (GDL).

A milk consisting of 9.5% dry matter, was inoculated with either YoFlex® Advance 2.0 or Glucono-δ-lactone (GDL) and PNGase-F as indicated in Table 3, heated to 43° C. and fermented to pH 4.55. After samples had been stored for 3 days at 5° C., the samples were stirred with a stirrer and poured into the rheometer cups and the rheology was measured according to example 2 and 3.

The results presented in table 3 confirmed that the effect of PNGase-F may be described as a physical phenomenon. The chemically acidified yogurt generates a much firmer gel than the Advance 2.0 culture. However, for both methods of acidification it is evident that the addition of PNGase-F improves the gel firmness.

TABLE 3

Experimental result of a 200 ml lab scale experiment of the preparation of a low fat yogurt in the presence of PNGase-F using either Advance 2.0 or GDL for acidification

|  | Concentration (U/ml milk) | Gel Firmness (Pa) |
|---|---|---|
| Advance 2.0 + PNGase-F | 250 | 35.3 ± 7.8 |
| Advance 2.0 | 0 | 24.7 ± 0.9 |
| GDL + PNGase-F | 250 | 148.0 ± 7.0 |
| GDL | 0 | 121.5 ± 6.4 |

Conclusions:

The results above demonstrated for both methods of acidification it is evident that the addition of PNGase-F improved the gel firmness.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. US2005/0095316A1 (Danone)
2. US2005/0095317A1 (Danone)
3. WO2007/095958A1 (Chr. Hansen A/S)
4. A. N. Hassan et al (J. Dairy Sci: 86:1632-1638; 2003)
5. U.S. Pat. No. 7,560,127B2 (DSM)
6. E. Cases et al (Journal of Food Science; Vol. 68, Nr. 8, 2003, Pages 2406-2410)
7. EP1489135A1
8. R. Scott, (1986), Cheesemaking process, second ed., Elsevier Applied Science Publishers, London and New York.
9. G. Bylund, (1995), Dairy processing handbook, Tetra Pak Processing Systems, Lund, Sweden
10. F. Kosikowski, (1982), Cheese and fermented milk foods, second ed., Kosikowski & Associates, New York All references cited in this patent document are hereby incorporated herein in their entirety by reference.

The invention claimed is:

1. A method for producing a fermented milk yogurt product comprising:
    (a) treating a milk substrate with an enzyme having O-linked glycosidase activity, and
    (b) fermenting the milk substrate with lactic acid bacteria,
    wherein the fermented milk yogurt product that has increased gel firmness relative to a fermented milk yogurt product produced with a comparable method but without the enzyme having O-linked glycosidase activity,
    wherein treating the milk substrate with the enzyme having O-linked glycosidase activity does not increase syneresis in the fermented milk product relative to a fermented milk yogurt product produced with a comparable method but without the enzyme having O-linked glycosidase activity, and
    wherein the enzyme having O-linked glycosidase activity is selected from α-N-acetyl-galactosaminidase (EC number: 3.2.1.49); α-galactosidase (EC number: 3.2.1.22); neuraminidase (EC number: 3.2.1.18); and combinations thereof.

2. The method of claim 1, wherein step (a) is performed before or during step (b).

3. The method of claim 1, wherein the milk substrate is selected from the group consisting of milk from animals and milk of plant origin.

4. The method of claim 3, wherein the milk from animals is from cows, sheep, ewes, goats, buffaloes, or camels.

5. The method of claim 3, wherein the milk of plant origin is soy milk, oak milk, rice milk, or almond milk.

6. The method of claim 1, wherein the the lactic acid bacteria belongs to a species selected from the group consisting of: *Streptococcus thermophilus, Lactobacillus delbrueckii* subsp. *bulgaricus, Lactococcus lactis, Lactococcus lactis* subsp. *cremoris, Leuconostoc mesenteroides* subsp. *cremoris, Pseudoleuconostoc mesenteroides* subsp. *cremoris, Pediococcus pentosaceus, Lactococcus lactis* subsp. *lactis* biovar. *diacetylactis, Lactobacillus casei* subsp. *casei,*

*Lactobacillus paracasei* subsp. *paracasei, Bifidobacterium bifidum*, and *Bifidobacterium longum*.

7. The method of claim 1, wherein $10^5$ to $10^{13}$ CFU/g of the lactic acid bacteria are added to the milk substrate.

8. A yogurt product obtained by the method of claim 1.

* * * * *